United States Patent
Anderson et al.

(10) Patent No.: US 11,485,967 B2
(45) Date of Patent: Nov. 1, 2022

(54) METHODS FOR CELL-FREE DNA EXTRACTION FOR NON-INVASIVE PRENATAL SCREENING

(71) Applicant: Quest Diagnostics Investments Incorporated, Wilmington, DE (US)

(72) Inventors: Ben Anderson, San Juan Capistrano, CA (US); Charles Strom, San Juan Capistrano, CA (US); David Tsao, San Juan Capistrano, CA (US); Yan Liu, San Juan Capistrano, CA (US); Weimin Sun, San Juan Capistrano, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 0 days.

(21) Appl. No.: 15/770,855

(22) PCT Filed: Oct. 25, 2016

(86) PCT No.: PCT/US2016/058640
§ 371 (c)(1),
(2) Date: Apr. 25, 2018

(87) PCT Pub. No.: WO2017/074926
PCT Pub. Date: May 4, 2017

(65) Prior Publication Data
US 2019/0127728 A1    May 2, 2019

Related U.S. Application Data

(60) Provisional application No. 62/246,421, filed on Oct. 26, 2015.

(51) Int. Cl.
*C12Q 1/6806* (2018.01)
*C12Q 1/686* (2018.01)
*C12N 15/10* (2006.01)

(52) U.S. Cl.
CPC ....... *C12N 15/1013* (2013.01); *C12Q 1/6806* (2013.01); *C12Q 1/686* (2013.01); *C12Q 2600/112* (2013.01); *C12Q 2600/16* (2013.01); *C12Q 2600/166* (2013.01)

(58) Field of Classification Search
CPC ............ C12Q 2563/149; C12Q 1/6806; C12Q 2523/308; C12Q 1/686; C12Q 2600/112; C12N 15/1013
See application file for complete search history.

(56) References Cited

U.S. PATENT DOCUMENTS

| | | |
|---|---|---|
| 6,649,419 B1 | 11/2003 | Anderson |
| 2013/0196322 A1 | 8/2013 | Domanico et al. |
| 2016/0312266 A1* | 10/2016 | Liu .............. C12Q 1/6816 |

FOREIGN PATENT DOCUMENTS

| | | |
|---|---|---|
| CN | 104164417 A | 11/2014 |
| CN | 104789553 A | 7/2015 |
| CN | 104946623 A | 9/2015 |
| WO | WO-2008/155549 A2 | 12/2008 |
| WO | WO-2013/045432 A1 | 4/2013 |
| WO | WO-2015/120445 A1 | 8/2015 |

OTHER PUBLICATIONS

Berensmeier, Sonja, "Magnetic particles for the separation and purification of nucleic acids," Appl. Microbiol. Biotechnol., vol. 73, pp. 495-504. (Year: 2006).*
Elkin et al., "High-Throughput Plasmid Purification for Capillary Sequencing," Genome Research, vol. 11, pp. 1269-1274. (Year: 2001).*
International Search Report as issued in corresponding International Application No. PCT/US2016/058640.
Jung et al., "Cell-free DNA in the blood as a solid tumor biomarker—A critical appraisal of the literature," Clinica chimica Acta, Nov. 11, 2010, 411(21-22):1611-1624.
Norton et al., "Non-Invasive Chromosomal Evaluation (NICE) Study: results of a multicenter prospective cohort study for detection of fetal trisomy 21 and trisomy 18," American Journal of Obstetrics & Gynecology, May 24, 2012, 207(2):137:e1-e8.
Perez-Campo et al., "Avoiding introduction of bias in the analysis of the methylation of free circulating DNA," Clinica Chimica Acta, Feb. 14, 2015, 444:206-207.
Stemmer et al., "Use of Magnetic Beads for Plasma Cell-free DNA Extraction: Toward Automation of Plasma DNA Analysis for Molecular Diagnostics," Clinical Chemistry, Nov. 1, 2003, 49(11):1953-1955.
Supplementary European Search Report dated Feb. 25, 2019, in EP 16860612.7.
Office Action and Search Report dated Apr. 9, 2021 in CN 201680076102.9, with English translation.
Chen, Yi, "The structure and principle of a magnetic bead purification and sorting system," Chinese Journal of Medical Device, May 15, 2014, 27(5):1-5, with English abstract.
Office Action and Supplemental Search Report dated Sep. 10, 2021 in CN 201680076102.9, with English translation.

* cited by examiner

*Primary Examiner* — Young J Kim
(74) *Attorney, Agent, or Firm* — Foley & Lardner LLP

(57) ABSTRACT

Provided herein are methods and systems for cell-free DNA extraction from liquid biological samples. The methods can be employed for determination of fetal DNA fraction and non-invasive prenatal screening of fetal aneuploidies and analyses of other types of cell-free DNA.

21 Claims, No Drawings

Specification includes a Sequence Listing.

```
                         SEQUENCE LISTING

<160> NUMBER OF SEQ ID NOS: 6

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (32)..(33)
<223> OTHER INFORMATION: Phosphorothioate linkage

<400> SEQUENCE: 1
acactctttc cctacacgac gctcttccga tct                                33

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (32)..(33)
<223> OTHER INFORMATION: Phosphorothioate linkage

<400> SEQUENCE: 2
gatcggaaga gcacacgtct gaactccagt cac                                33

<210> SEQ ID NO 3
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aatgatacgg cgaccaccga gatctacact ctttccctac acgacgctct tccgatct     58

<210> SEQ ID NO 4
<211> LENGTH: 68
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (25)..(34)
<223> OTHER INFORMATION: a, c, t, g, unknown or other

<400> SEQUENCE: 4
caagcagaag acggcatacg agatnnnnnn nnnngtgact ggagttcaga cgtgtgctct    60
tccgatct                                                            68

<210> SEQ ID NO 5
<211> LENGTH: 33
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (32)..(33)
<223> OTHER INFORMATION: Phosphorothioate linkage

<400> SEQUENCE: 5
acactctttc cctacacgac gctcttccga tct                                33

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(1)
<223> OTHER INFORMATION: 5' 5Phos modification
<220> FEATURE:
<221> NAME/KEY: misc_feature
<222> LOCATION: (32)..(33)
<223> OTHER INFORMATION: Phosphorothioate linkage

<400> SEQUENCE: 6
gatcggaaga gcacacgtct gaactccagt cac                                33
```

METHODS FOR CELL-FREE DNA EXTRACTION FOR NON-INVASIVE PRENATAL SCREENING

CROSS-REFERENCE TO RELATED APPLICATIONS

This application is a National Stage application of PCT/US2016/058640, filed Oct. 25, 2016, which claims priority from U.S. Provisional Application No. 62/246,421, filed Oct. 26, 2015.

The instant application contains a Sequence Listing which has been submitted in ASCII format via EFS-WEB and is hereby incorporated by reference in its entirety. Said ASCII copy, created on Jul. 19, 2018, is named sequence.txt and is 3 KB.

BACKGROUND OF THE INVENTION

Autosomal trisomies occur in approximately 1 in 500 live births. A majority of these trisomies occur at chromosomes 13, 18, and 21. Sex chromosome aneuploidies occur in approximately 1 in 500 live births. Current maternal serum screening markers only detect between 85 to 95% of chromosomal abnormalities and have a false positive rate up to 5 or 6%. Amniocentesis and CVS are a highly accurate method of determining chromosome abnormalities but they carry a procedure related risk of miscarriage. The risks often outweigh the benefit of the procedures and are not appropriate as a regular screening tool. The goal of non-invasive prenatal testing is to provide a screening tool that accurately detects genetic defects in a fetus without the risks associated with the traditional methods of fetal genetic testing.

Detection and quantification of fetal nucleic acid in maternal plasma is a non-invasive alternative method for prenatal genetic diagnosis. Effective diagnosis depends on the quantity and quality of the isolated DNA, which impacts the sensitivity and reproducibility of the assay.

SUMMARY OF THE INVENTION

Provided herein are methods of improving the quantity, quality and consistency of cell-free DNA (cfDNA) isolation from liquid biological samples. In particular embodiments, the liquid biological sample is obtained from a pregnant mammal (e.g., a human patient) for non-invasive prenatal diagnosis of a fetal aneuploidy.

In some embodiments, the methods provided can be applied to the diagnosis of cancer. In some embodiments, the liquid biological sample is obtained from a patient diagnosed as having cancer or is suspected of having cancer for isolation and detection of circulating tumor DNA. In some embodiments the test can be applied to a general population as a screening test to predict a risk of having cancer.

Provided herein, in certain embodiments, are methods for improving the yield of cell-free DNA (cfDNA) isolated from a liquid biological sample from a mammal, comprising separation of cfDNA from the sample using magnetic beads that reversibly bind the cfDNA and at least two types of magnetic separation steps for manipulation of the magnetic beads. For example, in some embodiments, the cfDNA is bound to the magnetic beads and the cfDNA-bound-magnetic beads are transferred from the sample tube to one or more vessels sequentially, e.g. a vessel containing a wash solution, or a vessel containing an elution solution. The eluted cfDNA is separated from the magnetic beads by contacting the outer surface of the vessel containing the elution solution containing the eluted cfDNA and the magnetic beads to a magnetic plate and collecting the elution solution containing the eluted cfDNA. In some embodiments, the magnetic plate comprises a ring magnet that causes the magnetic beads to adhere to the vessel walls so that the elution solution containing the eluted cfDNA can be collected.

Provided herein, in certain embodiments, are methods for isolating cell-free DNA (cfDNA) from a liquid biological sample from a mammal, comprising the following steps:
a) contacting a liquid biological sample containing cfDNA with a plurality of magnetic beads that reversibly bind to DNA;
b) separating the cfDNA-bound magnetic beads from the unbound components of the liquid biological sample;
c) transferring the cfDNA-bound magnetic beads to a vessel containing an elution solution;
d) separating the magnetic beads from the elution solution by contacting the vessel containing the cfDNA and the magnetic beads in the elution solution to a magnetic plate and collecting the elution solution containing the cfDNA.

In some embodiments, the cfDNA-bound magnetic beads are separated from the unbound components of the liquid biological sample by transferring the cfDNA-bound magnetic beads from the liquid biological sample to another vessel. In some embodiments, the cfDNA-bound magnetic beads are transferred from the liquid biological sample directly to the vessel containing the elution solution. In some embodiments, the cfDNA-bound magnetic beads are transferred from the liquid biological sample are transferred to a vessel containing a wash solution.

In some embodiments, the cfDNA-bound magnetic beads are transferred to a wash solution after step (b) and prior to step (c). In some embodiments, the cfDNA-bound magnetic beads are magnetically transferred to the wash solution. In some embodiments, the cfDNA-bound magnetic beads are transferred to two or more wash solutions, sequentially. In some embodiments, the cfDNA-bound magnetic beads are magnetically transferred to two or more wash solutions, sequentially. In some embodiments, the two or more wash solutions are the same. In some embodiments, the two or more wash solutions comprise two or more different wash solutions.

In some embodiments, the cfDNA-bound magnetic beads are separated from the unbound components of the liquid biological sample by inserting a rod-shaped magnet into the liquid biological sample to magnetically bind the cfDNA-bound magnetic beads, and depositing the magnetically-bound beads into another vessel. In some embodiments, the vessel contains a wash solution. In some embodiments, the vessel contains the elution solution.

In some embodiments, the cfDNA-bound magnetic beads are transferred to a wash solution by inserting a rod-shaped magnet into the liquid biological sample to magnetically bind the cfDNA-bound magnetic beads, and depositing the magnetically-bound beads into the vessel containing the wash solution.

In some embodiments, the cfDNA-bound magnetic beads are transferred to the elution solution in step (c) by inserting a rod-shaped magnet into the ethanol wash solution containing the cfDNA-bound magnetic beads, and depositing the magnetically-bound beads into the vessel containing the elution solution. In some embodiments, the washed cfDNA-bound magnetic beads are incubated in the elution solution for a sufficient time to elute the cfDNA from the magnetic beads. Suitable elution solutions release the bound cfDNA from the magnetic beads. Exemplary elution solution include water or buffers solutions such as a Tris buffer (e.g., 10 mM Tris, pH 7.0-8.0) or a TRIS-EDTA buffer.

In some embodiments, the rod-shaped magnet is surrounded by a tip cover such that the magnet does not directly contact the liquid biological sample, the wash solution or the elution solution.

In some embodiments, the transfer of the magnetic beads from one vessel to another vessel is automated.

In some embodiments, the surface of the magnetic beads comprises one or more functional groups that reversibly binds to DNA. In some embodiments, the magnetic beads comprise a magnetic metal oxide and a polymer. In some embodiments, the magnetic metal oxide is and oxide of iron, cobalt or nickel, or a combination thereof. In some embodiments, the polymer is cross-linked polystyrene. In some embodiments, the surface of the magnetic beads is coated with a silicon-containing coating. In some embodiments, the magnetic beads comprise a polymer core, a magnetic layer comprising the magnetic metal oxide covering the polymer, and a silicone containing outer layer covering the magnetic layer.

In some embodiments, the magnetic beads are uniform in diameter. In some embodiments, the magnetic beads are not uniform in diameter. In some embodiments, the magnetic beads are about 1 µm in diameter.

In some embodiments, the magnetic beads are incubated for a sufficient time to bind the cfDNA in the liquid biological sample to generate the cfDNA-bound magnetic beads.

In some embodiments, the magnetic plate contains a ring magnet.

In some embodiments, the liquid biological sample is a plasma sample. In some embodiments, the liquid biological sample is prepared by removal of cells from a blood sample.

In some embodiments, the liquid biological sample is obtained from a human subject.

In some embodiments, the liquid biological sample is obtained from a pregnant female.

In some embodiments, the volume of the liquid biological sample is 0.5-2 mL.

In some embodiments, the volume of the elution solution is less than 200 µl. In some embodiments, the volume of the elution solution is less than or about 150 µl, less than or about 100 µl, less than or about 90 µl, less than or about 80 µl, less than or about 70 µl, less than or about 60 µl, less than or about 50 µl, or less than or about 40 µl.

In some embodiments, the step (a) is performed in a multiwell plate. In some embodiments, the washing and elution steps are performed in the same-sized multi-well plate. In some embodiments, the multiwell plate is a 24-well deepwell plate.

In some embodiments, at least two duplicate liquid biological samples containing cfDNA are contacted with a plurality of magnetic beads. In some embodiments, the cfDNA-bound magnetic beads in each duplicate sample are pooled after step (a).

In some embodiments at least one of the two or more wash solutions is an ethanol wash solution. In some embodiments, the cfDNA-bound magnetic beads are transferred to the ethanol wash solution by inserting a rod-shaped magnet into the wash solution to magnetically bind the cfDNA-bound magnetic beads, and depositing the magnetically-bound beads into the vessel containing the ethanol wash solution. In some embodiments, the methods further comprise transferring the washed cfDNA-bound magnetic beads to a vessel containing a second ethanol wash solution.

In some embodiments, the washed cfDNA-bound magnetic beads are incubated in the elution solution for about 1 to about 10 minutes. In some embodiments, the washed cfDNA-bound magnetic beads are incubated in the elution solution for at least 4 minutes, for at least 5 minutes, for at least 6 minutes, for at least 7 minutes, for at least 8 minutes, for at least 9 minutes, or for at least 10 minutes. In some embodiments, heat is applied to the magnetic beads to elute the cfDNA.

DETAILED DESCRIPTION OF THE INVENTION

Certain Terminology

To facilitate an understanding of the present disclosure, a number of terms and phrases are defined below.

As used herein, unless otherwise stated, the singular forms "a," "an," and "the" also include the plural. Thus, for example, a reference to "an oligonucleotide" includes a plurality of oligonucleotide molecules, a reference to "a label" is a reference to one or more labels, a reference to "a probe" is a reference to one or more probes, and a reference to "a nucleic acid" is a reference to one or more polynucleotides.

As used herein, unless indicated otherwise, when referring to a numerical value, the term "about" means plus or minus 10% of the enumerated value.

As used herein, a "carrier" or "genetic carrier" is an individual having at least one copy of an allele of a genetic determinant that is involved in the expression of a particular phenotype.

The terms "amplification" or "amplify" as used herein includes methods for copying a target nucleic acid, thereby increasing the number of copies of a selected nucleic acid sequence. Amplification may be exponential or linear. A target nucleic acid may be either DNA or RNA. The sequences amplified in this manner form an "amplification product," also known as an "amplicon." While the exemplary methods described hereinafter relate to amplification using the polymerase chain reaction (PCR), numerous other methods are known in the art for amplification of nucleic acids (e.g., isothermal methods, rolling circle methods, etc.). The skilled artisan understands that these other methods may be used either in place of, or together with, PCR methods. See, e.g., Saiki, "Amplification of Genomic DNA" in PCR Protocols, Innis et al., Eds., Academic Press, San Diego, Calif. 1990, pp. 13-20; Wharam et al., Nucleic Acids Res., 29(11):E54-E54, 2001; Hafner et al., *Biotechniques,* 30(4): 852-56, 858, 860, 2001; Zhong et al., *Biotechniques,* 30(4): 852-6, 858, 860, 2001.

As used herein, the term "detecting" refers to observing a signal from a detectable label to indicate the presence of a target. More specifically, detecting is used in the context of detecting a specific sequence.

The terms "complement," "complementary" or "complementarity" as used herein with reference to polynucleotides (i.e., a sequence of nucleotides such as an oligonucleotide or a genomic nucleic acid) related by the base-pairing rules. The complement of a nucleic acid sequence as used herein refers to an oligonucleotide which, when aligned with the nucleic acid sequence such that the 5' end of one sequence is paired with the 3' end of the other, is in "antiparallel association." For example, for the sequence 5'-A-G-T-3' is complementary to the sequence 3'-T-C-A-5'. Certain bases not commonly found in natural nucleic acids may be included in the nucleic acids of the present disclosure and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs. Complementarity may be "partial" in which only some of the nucleic acids' bases are matched according to the base pairing rules. Or, there may be "complete," "total," or "full" complementarity between the nucleic acids.

The term "detectable label" as used herein refers to a molecule or a compound or a group of molecules or a group of compounds associated with a probe and is used to identify the probe hybridized to a genomic nucleic acid or reference nucleic acid.

A "fragment" in the context of a polynucleotide refers to a sequence of nucleotide residues, either double- or single-stranded, which are at least about 2 nucleotides, at least about 5 nucleotides, at least about 10 nucleotides, at least about 20 nucleotides, at least about 25 nucleotides, at least about 30 nucleotides, at least about 40 nucleotides, at least about 50 nucleotides, at least about 100 nucleotides.

The terms "identity" and "identical" refer to a degree of identity between sequences. There may be partial identity or complete identity. A partially identical sequence is one that is less than 100% identical to another sequence. Partially identical sequences may have an overall identity of at least 70% or at least 75%, at least 80% or at least 85%, or at least 90% or at least 95%.

As used herein, the terms "isolated," "purified" or "substantially purified" refer to molecules, such as nucleic acid, that are removed from their natural environment, isolated or separated, and are at least 60% free, at least 70% free, at least 80% free, at least 90% free, or at least 95% free from other components with which they are naturally associated. An isolated molecule is therefore a substantially purified molecule.

As used herein, the term "library" refers to a collection of nucleic acid sequences, e.g., a collection of nucleic acids derived from whole genomic, subgenomic fragments, cDNA, cDNA fragments, RNA, RNA fragments, or a combination thereof. In one embodiment, a portion or all of the library nucleic acid sequences comprises an adapter sequence. The adapter sequence can be located at one or both ends. The adapter sequence can be useful, e.g., for a sequencing method (e.g., an NGS method), for amplification, for reverse transcription, or for cloning into a vector.

The library can comprise a collection of nucleic acid sequences, e.g., a target nucleic acid sequence (e.g., a tumor nucleic acid sequence), a reference nucleic acid sequence, or a combination thereof). In some embodiments, the nucleic acid sequences of the library can be derived from a single subject. In other embodiments, a library can comprise nucleic acid sequences from more than one subject (e.g., 2, 3, 4, 5, 6, 7, 8, 9, 10, 20, 30 or more subjects). In some embodiments, two or more libraries from different subjects can be combined to form a library having nucleic acid sequences from more than one subject. In one embodiment, the subject is human having, or at risk of having, a cancer or tumor.

A "library nucleic acid sequence" refers to a nucleic acid molecule, e.g., a DNA, RNA, or a combination thereof, that is a member of a library. Typically, a library nucleic acid sequence is a DNA molecule, e.g., genomic DNA or cDNA. In some embodiments, a library nucleic acid sequence is fragmented, e.g., sheared or enzymatically prepared, genomic DNA. In certain embodiments, the library nucleic acid sequences comprise sequence from a subject and sequence not derived from the subject, e.g., adapter sequence, a primer sequence, or other sequences that allow for identification, e.g., "barcode" sequences.

The term "multiplex PCR" as used herein refers to amplification of two or more target nucleic acids which are each primed using a distinct primer pair.

"Next-generation sequencing or NGS" as used herein, refers to any sequencing method that determines the nucleotide sequence of either individual nucleic acid molecules (e.g., in single molecule sequencing) or clonally expanded proxies for individual nucleic acid molecules in a high throughput parallel fashion (e.g., greater than 103, 104, 105 or more molecules are sequenced simultaneously). In one embodiment, the relative abundance of the nucleic acid species in the library can be estimated by counting the relative number of occurrences of their cognate sequences in the data generated by the sequencing experiment. Next generation sequencing methods are known in the art, and are described, e.g., in Metzker, M. *Nature Biotechnology Reviews* 11:31-46 (2010).

As used herein, the term "oligonucleotide" or "polynucleotide" refers to a short polymer composed of deoxyribonucleotides, ribonucleotides, or any combination thereof. Oligonucleotides are generally between about 10, 11, 12, 13, 14, 15, 20, 25, or 30 to about 150 nucleotides (nt) in length, more preferably about 10, 11, 12, 13, 14, 15, 20, 25, or 30 to about 70 nt.

As used herein, a "primer" is an oligonucleotide that is complementary to a target nucleotide sequence and leads to addition of nucleotides to the 3' end of the primer in the presence of a DNA or RNA polymerase. The 3' nucleotide of the primer should generally be identical to the target sequence at a corresponding nucleotide position for optimal extension and/or amplification. The term "primer" includes all forms of primers that may be synthesized including peptide nucleic acid primers, locked nucleic acid primers, phosphorothioate modified primers, labeled primers, and the like. As used herein, a "forward primer" is a primer that is complementary to the anti-sense strand of DNA. A "reverse primer" is complementary to the sense-strand of DNA.

An oligonucleotide (e.g., a probe or a primer) that is specific for a target nucleic acid will "hybridize" to the target nucleic acid under suitable conditions. As used herein, "hybridization" or "hybridizing" refers to the process by which an oligonucleotide single strand anneals with a complementary strand through base pairing under defined hybridization conditions. It is a specific, i.e., non-random, interaction between two complementary polynucleotides. Hybridization and the strength of hybridization (i.e., the strength of the association between the nucleic acids) is influenced by such factors as the degree of complementary between the nucleic acids, stringency of the conditions involved, and the Tm of the formed hybrid.

"Specific hybridization" is an indication that two nucleic acid sequences share a high degree of complementarity. Specific hybridization complexes form under permissive annealing conditions and remain hybridized after any subsequent washing steps. Permissive conditions for annealing of nucleic acid sequences are routinely determinable by one of ordinary skill in the art and may occur, for example, at 65° C. in the presence of about 6×SSC. Stringency of hybridization may be expressed, in part, with reference to the temperature under which the wash steps are carried out. Such temperatures are typically selected to be about 5° C. to 20° C. lower than the thermal melting point (Tm) for the specific sequence at a defined ionic strength and pH. The Tm is the temperature (under defined ionic strength and pH) at which 50% of the target sequence hybridizes to a perfectly matched probe. Equations for calculating Tm and conditions for nucleic acid hybridization are known in the art.

As used herein, an oligonucleotide is "specific" for a nucleic acid if it is capable of hybridizing to the target of interest and not substantially hybridizing to nucleic acids which are not of interest. High levels of sequence identity are preferred and include at least 75%, at least 80%, at least 85%, at least 90%, at least 95% or at least 98% sequence identity. Sequence identity can be determined using a commercially available computer program with a default setting that employs algorithms well known in the art (e.g., BLAST).

The term "region of interest" refers to a region of a nucleic acid to be sequenced.

As used herein, the term "subject" refers to a mammal, such as a human, but can also be another animal such as a domestic animal (e.g., a dog, cat, or the like), a farm animal (e.g., a cow, a sheep, a pig, a horse, or the like) or a laboratory animal (e.g., a monkey, a rat, a mouse, a rabbit, a guinea pig, or the like). The term "subject" is used herein interchangeably with "individual" or "patient."

Overview

Detection and quantification of fetal nucleic acid in maternal plasma is a non-invasive alternative method for prenatal genetic diagnosis. Effective diagnosis depends on the quantity and quality of the isolated DNA, which impacts the sensitivity and reproducibility of the assay. Described herein are methods for improving the quantity and quality of cell-free nucleic acid (e.g., cell-free, cfDNA) isolated from liquid biological samples. The methods provide herein also reduce the sample-to-sample variation of isolated cfDNA (i.e., improve consistency of the cfDNA extraction process). The methods provided herein improve the accuracy of fetal fraction determination analysis and detection of fetal aneuploidies. The methods provided herein can also be applied to isolation and analysis of other forms of cell-free DNA, including circulating tumor DNA.

The cell-free nucleic acid may be isolated from any type of suitable liquid biological specimen or sample (e.g., a test sample). A sample or test sample can be any specimen that is isolated or obtained from a subject or part thereof (e.g., a human subject, a pregnant female, a fetus). Non-limiting examples of specimens include fluid from a subject, including, without limitation, blood or a blood product (e.g., serum, plasma, or the like), umbilical cord blood, amniotic fluid, cerebrospinal fluid, spinal fluid, lavage fluid (e.g., bronchoalveolar, gastric, peritoneal, ductal, ear, arthroscopic), washings of female reproductive tract, urine, feces, sputum, saliva, nasal mucous, prostate fluid, lavage, semen, lymphatic fluid, bile, tears, sweat, breast milk, breast fluid, the like or combinations thereof. In some embodiments, a liquid biological sample is a blood plasma or serum sample. The term "blood" as used herein refers to a blood sample or preparation from a pregnant woman or a woman being tested for possible pregnancy. The term encompasses whole blood, blood product or any fraction of blood, such as serum, plasma, buffy coat, or the like as conventionally defined. Blood or fractions thereof often comprise nucleosomes (e.g., maternal and/or fetal nucleosomes). Nucleosomes comprise nucleic acids and are sometimes cell-free or intracellular. Blood also comprises buffy coats. Buffy coats are sometimes isolated by utilizing a ficoll gradient. Buffy coats can comprise white blood cells (e.g., leukocytes, T-cells, B-cells, platelets, and the like). In certain embodiments buffy coats comprise maternal and/or fetal nucleic acid. Blood plasma refers to the fraction of whole blood resulting from centrifugation of blood treated with anticoagulants. Blood serum refers to the watery portion of fluid remaining after a blood sample has coagulated. Fluid samples often are collected in accordance with standard protocols hospitals or clinics generally follow. For blood, an appropriate amount of peripheral blood (e.g., between 3-40 milliliters) often is collected and can be stored according to standard procedures prior to or after preparation. A fluid sample from which nucleic acid is extracted may be acellular (e.g., cell-free). In some embodiments, a fluid or tissue sample may contain cellular elements or cellular remnants. In some embodiments, fetal cells or cancer cells may be included in the sample. In some embodiments the cells, cellular elements or cellular remnants was removed from the liquid sample prior to nucleic acid extraction.

A sample often is heterogeneous, by which is meant that more than one type of nucleic acid species is present in the sample. For example, heterogeneous nucleic acid can include, but is not limited to, (i) fetal derived and maternal derived nucleic acid, (ii) cancer and non-cancer nucleic acid, (iii) pathogen and host nucleic acid, or (iv) mutated and wild-type nucleic acid.

For prenatal applications of technology described herein, fluid sample can be collected from a female at a gestational age suitable for testing, or from a female who is being tested for possible pregnancy. Suitable gestational age may vary depending on the prenatal test being performed. In certain embodiments, a pregnant female subject sometimes is in the first trimester of pregnancy, at times in the second trimester of pregnancy, or sometimes in the third trimester of pregnancy. In certain embodiments, a fluid sample is collected from a pregnant female between about 1 to about 45 weeks of fetal gestation (e.g., at 1 -4, 4-8, 8-12, 12-16, 16-20, 20-24, 24-28, 28- 32, 32-36, 36-40 or 40-44 weeks of fetal gestation), or between about 5 to about 28 weeks of fetal gestation (e.g., at 6, 7, 8, 9,10, 1 1 , 12, 13, 14, 15, 16, 17, 18, 19, 20, 21 , 22, 23, 24, 25, 26 or 27 weeks of fetal gestation). In certain embodiments a fluid sample is collected from a pregnant female during or just after (e.g., 0 to 72 hours after) giving birth (e.g., vaginal or non-vaginal birth (e.g., surgical delivery)).

Methods for preparing serum or plasma from maternal blood are known. For example, a pregnant woman's blood can be placed in a tube containing EDTA or a specialized commercial product such as Streck BCT collection tubes (Streck), which stabilizes white blood cells, preventing the release of genomic DNA, allowing isolation of high-quality cell-free DNA, and plasma can then be obtained from whole blood through centrifugation. Serum may be obtained with or without centrifugation-following blood clotting. If centrifugation is used then it is typically, though not exclusively, conducted at an appropriate speed, e.g., 1,500-3,000 times g. Plasma or serum may be subjected to additional centrifugation steps before being transferred to a fresh tube for cfDNA extraction.

In some embodiments, the methods provided herein can be applied to the isolation of cell free DNA for the detection of circulating tumor DNA. Accordingly, in some embodiments, the subject is one that is diagnosed as having a cancer or is suspected of having a cancer.

Methods for Extracting Cell-Free DNA

The methods provided herein result in high quality and high yield cfDNA samples and reduce sample-to-sample variation of extracted cfDNA.

In the first step of the method, a liquid biological sample containing cfDNA is contacted with a plurality of magnetic solid phase particles, e.g. magnetic beads having a surface comprising one or more functional groups that reversibly binds to DNA. In some embodiments, the magnetic beads are coated with a silicon-based coating. In some embodiments, the magnetic beads are coated with a compound having a functional group that reversibly binds DNA.

Any, solid surfaces which bind DNA and have sufficient surface area to permit efficient binding can be used in the present methods. Microparticles, fibers, beads and supports contain suitable surfaces. Generally, magnetic beads are used in the present methods. In some embodiments, the magnetic microparticles used in the present methods comprise a magnetic metal oxide core, which is surrounded by an adsorptively or covalently bound silane coat to which a wide variety of bioaffinity adsorbents can be covalently bound through selected coupling chemistries, thereby coating the surface of the microparticles with functional groups. In some embodiments, the magnetic beads comprise a polymer. In some embodiments, the polymer is cross-linked polystyrene. In some embodiments, the surface of the magnetic beads is coated with a silicon-containing coating. In some embodiments, the magnetic beads comprise a polymer core, a magnetic layer comprising the magnetic metal oxide covering the polymer, and a silicon containing outer layer covering the magnetic layer. In some embodiments, the magnetic beads are uniform in size. In some embodiments, the magnetic beads are about 1μm in diameter.

In some embodiments, the magnetic metal oxide is iron oxide. In some embodiments, the iron oxide is a mixture of $Fe^{2+}$ and $Fe^{3+}$. $Fe^{2-}/Fe^{3+}$ ratio can vary from about 0.5:1 to about 4:1, such as, for example, 2:1. Suitable amino silanes useful to coat the microparticle surfaces include, but are not limited to, p-aminopropyltrimethoxysilane, N-2-aminoethyl-3-aminopropyltrimethoxysilane, triaminofunctional silane ($H_2NCH_2$—NH—$CH_2CH_2$—NH—$CH_2$—Si—$(OCH_3)_3$, n-dodecyltriethoxysilane and n-hexyltrimethoxysilane. Methods of preparing these microparticles are described in U.S. Pat. Nos. 4,628,037, 4,554,088, 4,672,040, 4,695,393 and 4,698,302, the teachings of which are hereby incorporated by reference into this application in their entirety. These patents disclose other amino silanes which are suitable to coat the iron oxide core or layer and which can be employed in the present methods.

In some embodiments, the volume of the liquid biological sample is about 0.5-2 mL. In some embodiments, a suitable binding buffer is added to the liquid biological sample prior to, following, or at the same time as contacting the sample with the magnetic solid phase particles. In some embodiments, the binding buffer contains a combination of chaotropic salts and detergents effective to release the cell-free DNA from any associated histones. Examples thereof include, but are not limited to, guanidinium (iso)thiocyanate, guanidine hydrochloride, sodium iodide, potassium iodide, sodium (iso)thiocyanate, urea or combinations thereof. In particular embodiments, the chaotropic salt is guanidinium (i so)thiocyanate.

The liquid biological sample and the magnetic solid phase particles are incubated for a sufficient time to bind the cfDNA in the liquid biological sample to generate cfDNA-bound magnetic solid phase particles. The cfDNA-bound magnetic solid phase particles are separated from the unbound components of the liquid biological sample by transferring the magnetic particles to a vessel containing a suitable wash solution. The wash buffer solution must have a sufficiently high salt concentration (i.e., has a sufficiently high ionic strength) that the DNA bound to the magnetic microparticles does not elute off of the microparticles, but remains bound to the microparticles. Suitable salt concentrations are greater than about 1.0 M and is preferably about 5.0 M. The buffer solution is chosen so that impurities that are bound to the DNA or microparticles are dissolved. The pH and solute composition and concentration of the buffer solution can be varied according to the type of impurities which are expected to be present. Suitable wash solutions include the following: a chaotropic guanidinium salt-containing wash buffer, 0.5×5 SSC; 100 mM ammonium sulfate, 400 mM Tris pH 9, 25 mM $MgCl_2$ and 1% bovine serum albumine (BSA); and 5M NaCl. The magnetic microparticles with bound DNA can also be washed with more than one wash buffer solution. The magnetic microparticles can be washed as often as required to remove the desired impurities. However, the number of washings is preferably limited to two or three in order to minimize loss of yield of the bound DNA.

In some embodiments, two or more wash steps are performed by transferring the magnetic particles to an additional vessel containing the wash solution for each additional wash. The washed cfDNA-bound magnetic solid phase particles are then transferred from the wash solution to a vessel containing an ethanol wash solution. In some embodiments, the ethanol wash solution is a 70%, 75%, 80%, 85%, or 90% ethanol solution. In some embodiments, two or more ethanol wash steps are performed by transferring the magnetic particles to an additional vessel containing the ethanol wash solution for each additional ethanol wash. The ethanol-washed cfDNA-bound magnetic particles are then transferred to a vessel containing an elution solution. Suitable elution solutions release the bound cfDNA from the magnetic beads. Exemplary elution solution include water or buffers solutions such as a Tris buffer (e.g., 10 mM Tris, pH 7.0-8.0) or a TRIS-EDTA buffer In some embodiments, the cfDNA-bound magnetic solid phase particles are transferred to vessels containing the various wash solutions and the elution solution by sequentially inserting a vertical rod-shaped magnet into the liquid sample containing the cfDNA-bound magnetic solid phase particles to magnetically bind the particles, and depositing the magnetically-bound solid phase particles into the next vessel containing the wash or elution solution. An exemplary vertical rod-shaped magnet for use in the present methods is described in U.S. Pat. No. 6,447,729. Typically the rod magnet is shielded with a plastic tip with low/no binding affinity for biomolecules (e.g. polypropylene). In some embodiments, the tip matches the shape of the multi-well plate (e.g. 24-well magnet tip comb for use with a 24 deep well plate, Kingfisher). This permits the magnet to retract from the tip, leaving the tip behind in the well which allows the release the magnetic particles into the recipient solution with low agitation. Once the magnetic particles are released, then the plastic tip can be removed from the well. Alternatively the plastic tip can remain in the well during mixing. For transfer of the magnetic particles to a subsequent vessel, the rod magnetic can be reapplied.

The separation of the magnetic solid phase particles from the elution solution containing the eluted cfDNA is accomplished by transferring the vessel containing the magnetic beads in the elution solution to a magnetic plate, for example a magnetic plate containing a ring magnet, and removing the elution solution containing the cfDNA. The elution solution containing the cfDNA is then removed from the vessel, leaving the magnetic solid phase particles behind. In some embodiments, heat is applied to the magnetic solid phase particles to elute the cfDNA.

In some embodiments, the volume of the elution solution is less than 200 µl. In some embodiments, the volume of the elution solution is less than or about 150 µl, less than or about 100 µl, less than or about 90 µl, less than or about 80 µl, less than or about 70 µl, less than or about 60 µl, less than or about 50 µl, or less than or about 40 µl. In some embodiments, the volume of the elution solution is about 70 µl.

In some embodiments, the cfDNA extraction method is performed using a multiwell plate. In some embodiments, the multiwell plate is a deepwell plate. In some embodiments, the multiwell plate is a 24-well deepwell plate.

One advantage of the present method is that multiple aliquots of the liquid biological sample can be contacted with the magnetic solid phase particles and the cfDNA-bound magnetic solid phase particles from each binding reaction can be combined prior washing. For example, the vertical rod-shaped magnet can be employed to collect the cfDNA-bound magnetic solid phase particles from each binding reaction prior to depositing all of the cfDNA-bound particles into the first wash solution. Accordingly, in some embodiments, at least two duplicate liquid biological samples containing cfDNA are contacted with a plurality of magnetic beads. In some embodiments, at least two or more duplicate liquid biological samples containing cfDNA are contacted with a plurality of magnetic beads. Such method improves the efficiency of the isolation steps and yield of the extracted cfDNA. This method differs from previous methods where aliquots of the liquid biological sample were processed separately or applied sequentially to the magnetic solid phase particles for binding. The present method allows for simultaneous binding and pooling of samples.

Another advantage of the present method is that final yield is improved and lower elution volumes can be used due to the step of applying a magnetic plate to the elution solution containing the magnetic solid phase particles in order to separate the magnetic particles from the eluted cfDNA. In prior methods, which use a vertical rod magnet for DNA extraction, the vertical rod magnet is employed for transfer of the magnetic solid particles to the wash solutions as well as removing the magnetic solid particles from the elution solution at the final elution step (see, e.g., King-Fisher® Flex System (Thermo Scientific)). In order to achieve acceptable consistent yields from such systems, higher elution volumes (500 µl), especially when using deepwell multiwell plates (e.g. 24-well deep well plates), are required (see www.thermo.com/kingfisher). Lower elution volumes lead to unrecoverable or insufficient eluted DNA. The lower elution volumes require that the tip height be lowered to contact the elution solution, which results in random bead smashing across the plate during mixing. It was found herein the this method leads to at least 5-10% of the wells having unrecoverable or insufficient eluted DNA after the removal of the beads. By contrast, the present method of using the plate magnet for the elution step produces high yields and high quality cfDNA with low sample-to-sample variability when using low elution volumes (e.g., less than 200 µl). Elution in a lower volume reduces the need for concentrating the sample for use in downstream library preparation steps and/or direct sequencing steps.

In some embodiments, the DNA extraction steps are automated. For example, a robotic arm is employed to transfer the magnetic beads from one vessel to another vessel. In some examples, an apparatus, such as a KingFisher™ Flex Magnetic Particle Processor (Thermo Scientific, Waltham, Mass.) equipped with a vertical rod-shaped magnet is used to collect the cfDNA-bound magnetic particles from the liquid biological sample and deposit the beads into the wash solutions and elution solutions.

Library Generation and Sequencing

In some embodiments, the extracted cfDNA is used to prepare an amplified library for high throughput sequencing. Typically, the cfDNA does not require fragmentation. In some embodiments, the cfDNA size ranges from about 150 bp to 200 bp. In some embodiments, the average size of the cfDNA is about 170 bp to about 175 bp.

In exemplary methods, the cell-free DNA is first be blunted and 5'-phosphorylated so that the cfDNA fragments can be ligated to adaptors. This process can be carried out with commercially available kits, such as the NEB Quick Blunting Kit® or NEBNext End Prep.

The prepared cfDNA fragments can then be ligated to nucleic acid adapters that permit nucleic acid amplification, target labeling, and/or sequencing. In some embodiments, a first adaptor is ligated the 5' end and/or 3' end of the prepared cfDNA fragment. In a particular embodiment, the first adaptor is a Y-shaped adaptor comprising two oligonucleotides that are partially complementary. Such adaptors permit differential labeling of the In some embodiments, the "forward" Y-shaped adapter sequence consists of or comprises:

(SEQ ID NO: 1)
ACACTCTTTCCCTACACGAC<u>GCTCTTCCGATC</u>*T or a sequence 90%, 95%, 97%, 98%, or 99% identical to SEQ ID NO:1. and the "reverse" Y-shaped adapter sequence consists of or comprises (SEQ ID NO: 2)
<u>GATCGGAAGAGC</u>ACACGTCTGAACTCCAGTCA*C or a sequence 90%, 95%, 97%, 98%, or 99% identical to SEQ ID NO:2. C*T in the "forward" sequence and A*C in "reverse" sequence are phosphorothioate bonds. The underlined sequence represents the complementary nucleotide sequences in each oligonucleotide. The neck portion (i.e., double-stranded portion) of the Y-shaped adaptor ends has a T overhang that permits ligation to the cfDNA fragments with a Blunt/TA ligase (NEB). The adaptor ligation reactions can be purified to remove unligated adaptors and other impurities using commercially available kit, e.g., Ampure® XP PCR Purification Beads (Beckman Coulter, #A63881) according to the manufacturer's protocol.

In some embodiments, the adapter ligated products are then amplified using a pair of amplification primers, where one amplification primer of the primer pair is a universal primer and the other primer of the primer pair bar coded reverse primer. The universal primer and/or bar-coded primer can provide a priming site for sequencing. The sequences can allow binding of a fragment to a flow cell for high throughput, massively parallel sequencing, as described herein.

In some cases, amplicons from a single sample source comprise an identical index sequence (also referred to as an index tag, a "barcode" or a multiplex identifier (MID)). In some cases, indexed amplicons are generated using primers (for example, forward primers and/or reverse primers) containing the index sequence. Such indexed primers may be included during library preparation as a "barcoding" tool to identify specific amplicons as originating from a particular sample source. Indexed amplicons from more than one sample source are quantified individually and then pooled prior to sequencing. As such, the use of index sequences permits multiple samples (i.e., samples from more than one sample source) to be pooled per sequencing run and the sample source subsequently ascertained based on the index sequence.

Exemplary universal forward primer and a bar coded reverse primers include the following primers:

P5 Universal:
(SEQ ID NO: 3)
AATGATACGGCGACCACCGAGATCTACACTCTTTCCCTACACGACGCTC

TTCCGATCT

MID Primer:
(SEQ ID NO: 4)
CAAGCAGAAGACGGCATACGAGAT<u>NNNNNNNNNN</u>GTGACTGGAGTTCAG

ACGTGTGCTCTTCCGATCT, where "NNNNNNNNNN" represent the molecular barcode sequence.

Any adapter sequence may be included in a primer used in the present invention.

In some embodiments, all forward amplicons (i.e., amplicons extended from forward primers that hybridized with antisense strands of a target segment) contain the same adapter sequence. In some embodiments when double stranded sequencing is performed, all forward amplicons contain the same adapter sequence and all reverse amplicons (i.e., amplicons extended from reverse primers that hybridized with sense strands of a target segment) contain an adapter sequence that is different from the adapter sequence of the forward amplicons.

Other adapter sequences are known in the art. Some manufacturers recommend specific adapter sequences for use with the particular sequencing technology and machinery that they offer.

In some embodiments, when adapter-ligated and/or indexed primers are employed to amplify a cfDNA fragment, the adapter sequence and/or index sequence gets incorporated into the amplicon (along with the target-specific primer sequence) during amplification. The presence of the index tag permits the differentiation of sequences from multiple sample sources.

In some embodiments, amplicons from more than one sample source are pooled prior to high throughput sequencing. "Multiplexing" is the pooling of multiple adapter-tagged and indexed libraries into a single sequencing run. When indexed primer sets are used, this capability can be exploited for comparative studies. In some embodiments, amplicon libraries from up to 48 separate sources are pooled prior to sequencing.

High throughput, massively parallel sequencing refers to sequencing methods that can generate multiple sequencing reactions of clonally amplified molecules and of single nucleic acid molecules in parallel. This allows increased throughput and yield of data. These methods are also known in the art as next generation sequencing (NGS) methods. NGS methods include, for example, sequencing-by-synthesis using reversible dye terminators, and sequencing-by-ligation.

In some embodiments, high throughput, massively parallel sequencing employs sequencing-by-synthesis with reversible dye terminators. In other embodiments, sequencing is performed via sequencing-by-ligation. In yet other embodiments, sequencing is single molecule sequencing.

Non-limiting examples of commonly used NGS platforms include Apollo 324™ NGS Library Prep System (IntengenX, Pleasanton, United States), Ion Torrent™ (Life Technologies, Carlsbad, Calif.), miRNA BeadArray (Illumina, Inc.), Roche 454™ GS FLXTM-Titanium (Roche Molecular Diagnostics, Germany), and ABI SOLiDTM System (Applied Biosystems, Foster City, Calif.). Following the production of an adapter tagged and, optionally indexed, amplicon library, the amplicons are sequenced using high throughput, massively parallel sequencing.

Determination of Cell-Free Fetal Fraction

Determining the fetal fraction in a male fetus is relatively simple as the amount of Y chromosome present as well as the magnitude of the observed normalized X chromosome read count deficit relative to female fetal samples can be used to directly calculate fetal fraction. Determining if fetal DNA from a female fetus is present is more difficult. Determining if female fetal DNA is present requires the analysis of the autosomes to determine its presence. Specific loci within the autosomes show an increase in cfDNA with a fetal origin. The degree of enrichment at these loci can be used to determine the presence of female fetal DNA.

Sequencing data generated by NGS methods performed on the cfDNA fragment libraries can be analyzed to determine cell-free fetal fraction, which distinguishes the portion of the cfDNA attributed to fetal DNA versus maternal DNA. Exemplary methods for determining fetal fraction include measuring the relative levels of either fetal specific, maternal specific, and/or male specific genes. Once the cell-free fetal fraction has been determined, the presence of particular aneuploidies can be assessed. Exemplary methods for determination of aneuploidies from NGS data are described, for example, in US2015/0005176. Sequenced reads are aligned to the reference human genome using a short read aligner. Aneuploidy is called if the number of reads mapped to each chromosome differs from its expectation based on a comparison with a set of baseline samples. The general approach is usually referred to as a read depth strategy. In cfDNA testing, the counts of specific cfDNA fragments arising from a particular chromosome are compared in euploid and trisomic pregnancies and the results are presented as Z-scores. The separation between the distributions of Z-scores from euploid and trisomic pregnancies increases with deeper levels of sequencing and an increasing fetal fraction. As demonstrated in the examples provided herein, performance of cfDNA extraction according to the methods provided results in a higher fetal fraction and consequently a higher Z score for accurate and sensitive prediction of fetal aneuploidy.

EXAMPLES

Example 1

NIPT Circulating Cell Free DNA Extraction

Whole blood from an expecting female contains both maternal cell free DNA (cfDNA) and fetal cfDNA. Whole blood is collected from the expecting mother in special blood collection tubes that prevent the maternal cells from lysing and releasing their DNA into the plasma. Preserving the maternal cells and preventing their DNA from entering the plasma prevents the ratio of fetal cfDNA to maternal DNA from dropping to a point where the fetal cfDNA would not be able to be detected. When the blood is received by the laboratory, it is centrifuged to separate the plasma, buffy coat and red blood cell portions. The cfDNA (both mother and fetus) is then extracted from the plasma portion of the whole blood.

The method described herein is performed to isolate the circulating cfDNA from maternal plasma samples by using magnetic beads that bind to the DNA in the sample (e.g., Dynabeads MyOne Silane). The extracted DNA is used for the downstream sequencing applications, for example, to test for the detection of specific chromosome disorders.

Dynabeads® MyOne™ SILANE are uniform, monosized ferromagnetic beads, 1 in diameter. The beads are composed of highly cross-linked polystyrene with evenly distributed magnetic material. The beads are further coated, enclosing the iron oxide inside the beads and presenting a bead surface with optimized silica-like chemistry. The increased magnetic strength of these beads ensure rapid magnetic mobility and efficient isolation of nucleic acids (DNA/RNA). The beads also feature a low sedimentation rate and favorable reaction kinetics, making them particularly suited for automated assays. (See Product Description for Dynabeads® MyOne™ SILANE, Life Technologies)

Each maternal blood sample is collected in two Streck BCT Collection Tubes and stored at ambient temperature for up to 4 days. The plasma is then isolated by spinning the samples twice. The reagent and plasma sample plates are first prepared on the Hamilton Microlab STAR liquid handler (Hamilton Company, Reno, Nev.). Then the prepared plates plus one comb plate are loaded on the KingFisher™ Flex Magnetic Particle Processor (with 24 Deep-well head) (Thermo Scientific, Waltham, Mass.) for DNA extraction. Circulating DNA is effectively released from histone wrap with a unique combination of chaotropic salts and detergents at room temperature.

The free dsDNA binds to Silane magnetic beads and then the DNA bound beads are collected on the comb with magnetic rod inserted into the center of the comb. After several washes, the non-specifically bound proteins are washed off. The Silane beads are released from the comb and the dsDNA is eluted in a DNA elution buffer. Finally, the KingFisherTM DNA Elution plates containing the magnetic beads still in the elution buffer are transferred to magnetic plates containing ring magnets on a Hamilton Microlab Starlet, which transfers the eluted DNA solution into a DNA collection plate which is then stored at −20° C. until use. A detailed description of the DNA extraction protocol follows.

Protocol

Whole blood samples (approximately 20 mL) from patients are collected in Streck BCT collection tubes (Streck, Ct #218962, approximately 10 mL per tube, two tubes per patient). The samples are shipped to the processing laboratory at ambient temperature (18-26° C.). For optimum results, the samples are received at the laboratory within 4 days of collection from the patients.

The Streck tubes are centrifuged at 2,500×g (RCF) for 10 minutes at 22° C. in round bottom bucket adaptors. After the centrifugation is completed, the Streck tubes are transferred to a safety hood without disturbing the buffy coat layer. The plasma is collected from each tube without touching the buffy coat. Plasma from each patient's respective two Streck tubes are pooled into a first conical tube (tube #1). After removal of the plasma, the Streck tubes are recapped with their original stoppers and the leftover material is stored at 4° C.

The conical tubes are centrifuged at 3,200×g (RCF) for 20 minutes at 22° C. in conical bottom bucket adaptors. After the centrifugation is completed, the plasma is collected. 4.5 mL of the collected plasma is transferred to a second conical tube (tube #2) and the remainder collected plasma to a third conical tube (tube #3) for backup. The cell pellets remaining in conical tube #1 are discarded. For same day extraction of DNA, plasma tube #2 is stored at 4° C. For longer term storage, the tubes are stored at −20° C. or lower until use.

Before DNA extraction, if the plasma is still frozen, the plasma is thawed at room temperature. Once thawed, the plasma tubes are centrifuged at 3,000×g (RCF) for 10 minutes. Any tubes with plasma less than 3 mL are recorded.

The Dynabeads Binding Solution stock is then prepared. The container of Dynabeads® MyOne™ SILANE (Life Technologies—Cat no. 37002D) is removed from the refrigerator and vortexed vigorously for 1 minute just before adding to the DynaMax Binding Solution (DynaMax Cell Free DNA Extraction Kit, Cat no. 4479983). 1500 μL of Dynabeads® MyOne™ SILANE magnetic beads are added to 125 mL of DynaMax Binding Solution (DynaMax Cell Free DNA Extraction Kit, Cat no. 4479983) to generate a Dynabeads Binding Solution stock.

The following sets of 24-deep-well plates (KingFisher™ Flex 24 Deep Well Plate, Molecular BioProducts Inc., Cat no. 95040480) are prepared using a Hamilton Microlab STAR liquid handler (Hamilton Company, Reno, Nev.):

1) 2 mL of patient plasma sample plus 2 mL Dynabeads Binding Solution stock (prepared above) (4 mL total volume).

2) Duplicate of plate #1.

3) 1 mL DynaMax Wash Solution (DynaMax Cell Free DNA Extraction Kit, Cat no. 4479983)

4) 1 mL DynaMax Wash Solution (DynaMax Cell Free DNA Extraction Kit, Cat no. 4479983)

5) 2 mL 80% Ethanol 6) 600 ∥l 80% Ethanol

7) DynaMax Elution Solution (DynaMax Cell Free DNA Extraction Kit, Cat no. 4479983)

The prepared plates are then unloaded from the Hamilton Microlab STAR and checked for consistency of reagent volumes. The prepared plates are then loaded onto a KingFisher™ Flex Magnetic Particle Processor (with 24 Deep-well head) (Thermo Scientific, Waltham, Mass.). A plate containing the KingFisher™ Flex 24 Deep Well Tip Comb (Molecular BioProducts Inc.—Cat no. 97002610) also is loaded onto the KingFisher™ processor. During the individual steps, the plates are kept stationary, and the only moving assembly is the processing head with tip comb and magnetic rods. The head consists of two vertically moving platforms. One platform moves the plastic tip comb in and out of the deep-well sample plates, and the other platform moves the magnetic rods in and out of the plastic tip comb. The operating principle employed to DNA extraction is called inverse magnetic particle processing (MPP) technology. Rather than moving the liquids to and from the plates as is done with an external magnet method, the magnetic particles themselves are moved from plate to plate containing specific reagents. Magnetic particles are transferred to each sequential plate (#1-#7) with the aid of magnetic rods covered with the disposable, specially designed plastic tip comb.

The program for isolation of the cfDNA from the plasma samples proceeds as follows: 1) collection of cfDNA bound to the magnetic particles of plate #1 (i.e. binding of the DNA bound magnetic particles to the comb by inserting the comb and magnet rod assembly into the wells of plate #1); 2) collection of cfDNA bound to the magnetic particles of plate #2 (i.e., DNA bound magnetic particles in plate #2 also become bound to the comb); 3) first wash with DynaMax Wash Solution; 4) second wash with DynaMax Wash Solution; 5) first 80% Ethanol Wash; 6) second 80% ethanol wash; and 7) elution with 70 µl DynaMax Elution Solution. In between each step, the beads are released from the comb by removal of the magnetic rod from the comb assembly, and re-bound by insertion of the magnetic rod into the comb assembly.

Under standard operation, the KingFisher™ processor removes the beads from the elution buffer during step 7 when the beads are deposited into the elution buffer, which would leave the purified liquid sample containing the cfDNA behind. It was found that 5-10% of the wells has unrecoverable or insufficient eluted DNA when less than 100 µl of the elution solution was used. For the reminder of the wells, less than 50 µl was typically recovered from a 70 µl elution. These poor results was likely due to bead smashing that occurs during the depositing and mixing of the beads in the low elution volumes.

The current method modifies the standard KingFisher™ DNA purification protocol in that the beads are not removed from the elution solution during step 7, thus allowing a smaller elution volume to be used. The beads are released into the elution solution plate (#7) for the elution step and then the elution plate, still containing the beads and the elution solution, is moved to a 24-well magnetic plate having ring magnets. The ring magnets bind the beads to the sides of the wells, thus allowing a more complete removal of the eluted sample. This modified step of switching to a ring magnet for collection of the eluted sample significantly increases the yield of cfDNA in the final sample and allows for a much smaller elution volume. In addition that current method result in 100% recovery of at least 65 µl of the 70 µl elution.

The magnetic plates containing the ring magnets are positioned in a Hamilton Microlab STARlet liquid handler. Once binding of the magnetic beads has occurred, the eluted sample containing the cfDNA is transferred to a 96 well plate using the liquid handler.

Example 2

Sequencing of cfDNA Samples

In this example, the extracted cfDNA from Example 1 is prepared for sequencing. The extracted DNA is amplified and sample specific barcodes are attached to the cfDNA fragments. The amplified products are then analyzed using massively parallel sequencing technology (also called next-generation sequencing (NGS)). The data from the sequencer is then analyzed and a report is generated for chromosomes 13, 18, 21, X and Y which will tell the copy number of those chromosomes present in the fetal sample. This assay is able to detect Patau Syndrome (trisomy 13), Edwards Syndrome (trisomy 18), Down Syndrome (trisomy 21) as well as sex chromosome abnormalities such as Turners Syndrome (X) and Kleinfelters Syndrome (XXY).

Protocol

Cell-free DNA is extracted according to the methods described in Example 1. A library is then prepared from the extracted cfDNA according to the following protocol using the NEBNext® Ultra™ DNA Library Prep Kit for Illumina® (New England BioLabs, #E7370B). For automated aliquotting of reagents, the Hamilton Starlet Liquid Handler is used.

End Repair

For end repair of cfDNA fragments, NEBNext End Prep Reaction is prepared. NEBNext End Prep Reagents are thawed on a cold block and aliquotted as follows.

TABLE 1

| NEBNext End Prep | Cocktail x1 (uL) | Cocktail x110 (uL) |
| --- | --- | --- |
| End Repair Reaction Buffer (10X) | 6.5 | 715 |
| End Prep Enzyme Mix | 3.0 | 330 |
| Total Master Mix | 9.5 | 1,045 |

127 µL NEBNext End Prep Master Mix is manually aliquotted to each well an 8-strip PCR tube on a cold block. 9.5 µL NEBNext End Prep Master Mix is then transferred from the 8-strip tubes to each well of a 96-well PCR plate using the Hamilton Starlet Liquid Handler. 55.5 µL of the extracted cfDNA is also transferred to the 96-well PCR plate (Total reaction volume 65 µL. The PCR plate is sealed with a foil seal, vortexed briefly (approximately 5 seconds) and spun down for approximately 5-15 seconds in a plate centrifuge at 2,000-6,000 rcf (1,600 rpm in a Sorvall T6000D centrifuge or equivalent).

The PCR plate is then placed in a thermal cycler and incubated under the following conditions.

TABLE 2

| 1 | 20° C. | 30 minutes |
| --- | --- | --- |
| 2 | 65° C. | 30 minutes |
| 3 | 4° C. | Hold |

The 96 well plate is then removed from the thermal cycler and spun down for approximately 5-15 seconds in a plate centrifuge at 2,000-6,000 rcf (1,600 rpm in a Sorvall T6000D centrifuge or equivalent).

Adapter Ligation

Y shaped NIPT Adaptors are generated from the following oligonucleotides, NIPTAdaptor1 and NIPTAdaptor2:

```
NIPTAdaptor1:
                                       (SEQ ID NO: 5)
ACACTCTTTCCCTACACGACGCTCTTCCGATC*T NIPTAdaptor2:
                                       (SEQ ID NO: 6)
/5Phos/GATCGGAAGAGCACACGTCTGAACTCCAGTCA*C
```

C*T in NIPTAdaptor1 and A*C in NIPTAdaptor2 are phosphorothioate bonds. The underlined sequence represents the complementary nucleotide sequences in each oligonucleotide. Stock NIPT Adaptors containing the hybridized NIPTAdaptor1 and NIPTAdaptor2 are prepared at a 50 µM concentration according to the following table.

TABLE 3

| Stock NIPT Adapter | Cocktail x1 (uL) | Cocktail x300 (uL) |
| --- | --- | --- |
| NIPTAdapter1 (150 µM) | 0.835 | 250.5 |
| NIPTAdapter2 (150 µM) | 0.835 | 250.5 |
| 5M NaCl | 0.05 | 15 |
| 1X TE | 0.25 | 75 |
| Water | 0.53 | 159 |
| Total | 2.5 | 750 |

50 µL of the Stock NIPT Adapter Mix is aliquotted into each well of a new 96-well PCR Plate. The plate is sealed, placed in a thermal cycler and incubated under the following conditions:

TABLE 4

| Step | Temperature | Time | Ramp % |
|---|---|---|---|
| 1 | 95° C. | 5 min | 100 |
| 2 | 35° C. | 1 sec | 10 |
| 3 | 25° C. | 5 min | 40 |
| 4 | 4° C. | Hold | 100 |

When the program is complete, all wells are combined back into one single sterile microcentrifuge tube and pulse vortexed 5-10 times. For storage, 30 uL volumes are aliquotted into sterile microcentrifuge tubes, and stored at −15° C. to −25° C.

The Adaptor Ligation Master mix is prepared according to the following amounts:

TABLE 5

| Adapter Ligation | Cocktail x1 (uL) | Cocktail x115 (uL) |
|---|---|---|
| Blunt/TA Ligase Master Mix | 15 | 1,725 |
| Ligation Enhancer | 1 | 115 |
| Stock NIPT Adapter (50 uM) | 0.083 | 9.55 |
| Water | 2.417 | 277.95 |
| Total | 18.5 | 2,128 |

259 µL Adaptor Ligation Master mix is manually aliquotted to each well an 8-strip PCR tube on a cold block. 18.5 µL Adaptor Ligation Master mix is then transferred from the 8-strip tubes to each well the End Prep PCR plate using the Hamilton Starlet Liquid Handler (Total volume=83.5 µL. The PCR plate is sealed with a foil seal, vortexed briefly (approximately 5 seconds) and spun down for approximately 5-15 seconds in a plate centrifuge at 2,000-6,000 rcf (1,600 rpm in a Sorvall T6000D centrifuge or equivalent).

The PCR plate is then placed in a thermal cycler and incubated under the following conditions.

TABLE 6

| 1 | 20° C. | 15 minutes |
|---|---|---|
| 2 | 4° C. | Hold |

The 96 well plate is then removed from the thermal cycler and spun down for approximately 5-15 seconds in a plate centrifuge at 2,000-6,000 rcf (1,600 rpm in a Sorvall T6000D centrifuge or equivalent).

AMPure Clean-Up of Ligation Product

The adaptor ligation reactions are then purified to remove unligated adaptors and other impurities using Ampure® XP PCR Purification Beads (Beckman Coulter, #A63881) according to the manufacturer's protocol. Aliquotting steps of the method were performed using the Hamilton Starlet Liquid Handler.

Briefly, 83.5 µL AMPure XP beads are added to the Ligation product plate, mixed, and incubated 10 minutes at room temperature for DNA binding. The plate is then transferred onto a magnetic plate, and let sit 4 minutes to clear the supernatant. The supernatant is then removed and discarded. 180 µL of freshly prepared 80% ethanol is added, incubated for 30 seconds and then removed and discarded. The 80% ethanol wash is repeated 2 more times (3 washes total). After removal of last ethanol wash, the beads air dried on the magnet plate for 2 minutes. The plate is then removed from the magnet. 28 µL water is added to resuspend the beads and incubated 2-5 minutes at room temp to elute DNA. The plate is then transferred back to magnet, let sit 2 minutes clear the elution solution. 23 µL of the supernatant (purified DNA) is then transferred to a new 96-well PCR plate.

PCR of Library

The adapter ligated products are then amplified using a universal forward primer and a bar coded reverse primer.

P5 Universal:
(SEQ ID NO: 3)
AATGATACGGCGACCACCGAGATCTACACTCTTTCCCTACACGACGCT

CTTCCGATCT

MID Primer:
(SEQ ID NO: 4)
CAAGCAGAAGACGGCATACGAGAT<u>NNNNNNNNNN</u>GTGACTGGAGTTCA

GACGTGTGCTCTTCCGATCT (The underlined portion of the MID primer represents the unique 10 nucleotide molecular ID sequence). Exemplary barcode sequences can be found for example in US 20140141436 and (Attorney Docket No. 034827-0803).

The PCR Master Mix is prepared according to the following amounts. The MID barcoded primers are aliquotted separately.

TABLE 7

| PCR Master Mix | Cocktail x1 (uL) | Cocktail x120 (uL) |
|---|---|---|
| NEBNext HiFi 2X PCR Master Mix | 25 | 3,000 |
| Universal Primer (10 uM) | 1 | 120 |
| Total | 26 | 3,120 |

26 µL PCR master mix is added directly to each well of the cleaned up ligation plate (total volume=50 µL). 2 µL of the appropriate MID primer (5 µM) is aliquotted to each well of the PCR plate. A different barcode is aliquotted into each well of the plate. The PCR plate is sealed with a foil seal, vortexed briefly (approximately 5 seconds) and spun down for approximately 5-15 seconds in a plate centrifuge at 2,000-6,000 rcf (1,600 rpm in a Sorvall T6000D centrifuge or equivalent).

The PCR plate is then placed in a thermal cycler and incubated under the following conditions.

TABLE 8

| Step | Temperature | Time | |
|---|---|---|---|
| 1 | 98° C. | 30 sec | |
| 2 | 98° C. | 10 sec | 10 |
| 3 | 65° C. | 30 sec | cycles |
| 4 | 72° C. | 30 sec | |
| 4 | 72° C. | 5 min | |
| 4 | 4° C. | Hold | |

The 96 well plate is then removed from the thermal cycler and spun down for approximately 5-15 seconds in a plate centrifuge at 2,000-6,000 rcf (1,600 rpm in a Sorvall T6000D centrifuge or equivalent).

Clean-Up of Library PCR Product

The Library PCR reactions are then purified to remove primers and other impurities using Ampure® XP PCR Purification Beads (Beckman Coulter, #A63881) according to the manufacturer's protocol. Aliquotting steps of the method were performed using the Hamilton Starlet Liquid Handler.

Briefly, 50 µL AMPure XP beads are added to the Ligation product plate, mixed, and incubated 5 minutes at room temperature for DNA binding. The plate is then transferred onto a magnetic plate, and let sit 3 minutes to clear the supernatant. The supernatant is then removed and discarded. 180 µL of freshly prepared 80% ethanol is added, incubated for 30 seconds and then removed and discarded. The 80% ethanol wash is repeated 2 more times (3 washes total). After removal of last ethanol wash, the beads air dried on the magnet plate for 2 minutes. The plate is then removed from the magnet. 33 µL water is added to resuspend the beads and incubated 2-5 minutes at room temp to elute DNA. The plate is then transferred back to magnet, let sit 2 minutes clear the elution solution. 28 µL of the supernatant (purified DNA) is then transferred to a new 96-well PCR plate.

The amplified library is quantitated using Quant-It PicoGreen® dsDNA Assay Kit (Invitrogen, #P7589) according to the manufacturer's protocol. The molar concentration of the library samples is calculated based on an average library size of 298 bp. Thus, the molecular weight of the library is approximately 193,700 g/mol (298 bp×650 g/mol per bp).

After quantitation of the amplified library, the library is normalized with water to 2 nM. The library is pooled across each row of the 96-well plate (5 µL/well) to yield 8 pools of 60 µL each for each 96-well plate.

NGS Sequencing

The normalized pooled libraries are then prepared for NGS sequencing using the HiSeq SR Cluster Kit v4 cBot, which includes a high-output single-read flow cell, cBot clustering reagents, and indexing reagents. Flow Cell Clustering on the cBot reagent plate is performed according to the manufacturer's instructions. High Output Sequencing is then performed using the Illumina HiSeq 2500 and Hi Seq SBS Kit v4 according to the manufacturer's instructions.

The following control samples were used for each sequencing run:

1) PhiX Sequencing Control

A low level spike in, 5%, of a control library generated from the PhiX virus is added to the sequencing pool before cluster generation and loading on the HiSeq for sequencing. This allows the Illumina cluster detecting algorithms to perform better due to a more balanced representation of A,T,G and C nucleotides. This also helps to determine on a failed HiSeq run if the failure was in sample preparation or in cluster generation on the flow cell. Since the PhiX sequence is known, this spike in also helps determine the error rate of the run and provides an indication of sequencing success. Phasing and prephasing rate is also determined using the PhiX sequence.

2) Pooled Negative Plasma Control

A mixture of previously run remnant plasma is mixed together and the fetal fraction for that combined mixture is determined. The pooled plasma is aliquotted out into single uses and stored frozen until use. One of these controls is run on each 96 well plate and used as a control for the whole assay protocol. The known fetal fraction for the control should match with the calculated fetal fraction for each run 3) Positive Control A positive control is added during multiplexing. This control is generated by combining library amplified products, each with a different barcode attached to it, that includes a normal euploid sample with a 5% mixture of each Trisomy 21, Trisomy 18 and Trisomy 13.

4) Negative DNA Controls

Negative DNA Controls include the following: a) NS (No Sample) Control: A reagent blank which includes the reagents used to extract the sample DNA. If samples are prepared on separate occasions, a reagent blank control must be included for each individual preparation. b) ND Control: A minus DNA control (ND control) must be placed at the end of the run. This control consists of PCR kit and polymerase mix used for the assay run.

Alignment and analysis of sequence reads is performed using proprietary software. Z-scores are calculated based on each sample-chromosome pair (i.e., for chromosomes 21, 18 and 13). Exemplary Z-score data for pre-validation studies with known Trisomy 21 positives using the cfDNA extraction method, constructed samples, and normal samples are shown in Table 9.

TABLE 9

| Sample ID | Z-score | Composition of constructed/normal samples |
|---|---|---|
| Q0256_MID039 | 13.48461293 | |
| Q00352_MID039 | 12.94768903 | |
| Q01407_MID024 | 13.24801795 | |
| Q00082_MID073 | 12.80022514 | |
| Q01319_MID027 | 12.63944832 | |
| Q00084_MID074 | 12.71152341 | |
| Q00083_MID074 | 11.39330754 | |
| Q00527_MID051 | 11.27868636 | |
| Q01408_MID025 | 11.23511941 | |
| Q00614_MID047 | 7.711804345 | |
| Q01056_MID035 | 6.1944683 | |
| Q12378_S12_L001 | 6.001329598 | T21 3% constr |
| Q01143_MID032 | 5.317069393 | SQNM FF = 3.973 |
| Q11498_MID384 | 5.143841863 | T21 4% constr |
| Q11497_MID383 | 4.857682003 | T21 3% constr |
| Q12377_S24_L002 | 2.974488931 | T21 2% constr |
| Q01504_MID029 | 2.086359525 | Norm |
| Q00305_MID375 | 1.823235865 | Norm |
| Q00373_MID061 | 1.299134458 | Norm |

Table 10 shows exemplary validation results for Chromosome 13, 18 and 21 aneuploidies using two quality control metrics, either a read count threshold alone (i.e. 9 million reads) or the read count in combination with a percentage of reads mapped to the genome.

TABLE 10

| Sensitivity/Specificity Using ONLY Read Count Threshold | | | |
|---|---|---|---|
| | Chr 13 | Chr 18 | Chr 21 |
| True Positive | 4 | 10 | 15 |
| True Negative | 368 | 362 | 355 |
| False Positive | 0 | 0 | 0 |
| False Negative | 0 | 0 | 0 |
| Total Samples | 372 | 372 | 370 |
| Sensitivity | 100.0% | 100.0% | 100.0% |
| Specificity | 100.0% | 100.0% | 100.0% |

| Sensitivity/Specificity Using Read Count and % Mapped Thresholds | | | |
|---|---|---|---|
| | Chr 13 | Chr 18 | Chr 21 |
| True Positive | 4 | 9 | 15 |
| True Negative | 367 | 362 | 354 |
| False Positive | 0 | 0 | 0 |
| False Negative | 0 | 0 | 0 |
| Total Samples | 371 | 371 | 369 |
| Sensitivity | 100.0% | 100.0% | 100.0% |
| Specificity | 100.0% | 100.0% | 100.0% |

For the pre-validation studies, perfect intra-assay concordance was observed among at least five replicates for an exemplary negative sample and an exemplary Trisomy 21 positive sample.

Table 11 shows exemplary validation data for Z-scores and fetal fraction for multiple gestation pregnancy samples.

TABLE 11

| Flowcell | Sample | Z.Mean.Mad | Concordant | FF |
|---|---|---|---|---|
| T13 | | | | |
| AC6G9R | MF0116_MID040 | 11.14954337 | Yes | 12.49 |
| T18 | | | | |
| AC6G9R | MF0111_MID038 | 30.55752229 | Yes | 10.98 |
| AC6G92 | MF114_MID039 | 23.45230739 | Yes | 20.17 |
| AC6G9R | MF0112_MID039 | 12.81936655 | Yes | 7.63 |
| AC6G92 | MF113_MID038 | 10.64368517 | Yes | 9.21 |
| T21 | | | | |
| AC6G92 | MF106_MID037 | 26.64485662 | Yes | 14.23 |
| AC6G9R | MF0101_MID035 | 16.80828463 | Yes | 14.2 |
| AC6G9R | MF0103_MID037 | 15.1580532 | Yes | 13.55 |
| AC6G78 | MF0108_MID037 | 14.66836417 | Yes | 8 |
| AC6G78 | MF0107_MID036 | 13.13026839 | Yes | 8.66 |
| AC6G9R | MF0102_MID036 | 12.37312038 | Yes | 8.62 |
| AC6G78 | MF0110_MID039 | 12.19752486 | Yes | 10.94 |
| AC6G92 | MF0105_MID036 | 11.52830058 | Yes | 10.77 |
| AC6G92 | MF0104_MID035 | 9.452609754 | Yes | 13.17 |
| AC6G78 | MF0109_MID038 | 8.033323435 | Yes | 7.77 |

Table 12 shows exemplary test data for Z scores for selected positive samples showing aneuploidies in chromosomes 13, 18 and 21. The average Z scores for wt/wt samples were -0.3 for T13, -0.06 for T18 and -0.06 for T21.

TABLE 12

| Sample ID | chr21 | Sample ID | chr18 | Sample ID | chr13 |
|---|---|---|---|---|---|
| 67031233_MID064 | 22.8 | 60586177_MID047 | 33.2 | 338_MID059 | 12.2 |
| 73184290_MID034 | 19.0 | 460_MID378 | 21.8 | 282_MID001 | 16.4 |
| 68149202_MID026 | 26.9 | NIPT15-609_MID055 | 48.0 | NIPT15-645_MID381 | 10.8 |
| 295_MID015 | 12.6 | NIPT15-637_MID373 | 9.3 | NIPT15-1531_MID372 | 59.1 |
| 284_MID004 | 24.1 | NIPT15-460_MID048 | 22.2 | NIPT15-2589_MID004 | 10.3 |
| 439_MID068 | 39.0 | NIPT15-1635_MID004 | 15.8 | NIPT15-2715_MID040 | 10.4 |
| 452_MID370 | 19.5 | NIPT15-1363R_MID383 | 12.1 | | |
| NIPT15-493_MID029 | 18.2 | NIPT15-2886_MID039 | 13.3 | | |
| NIPT15-588_MID033 | 15.0 | NIPT15-3016_MID005 | 24.3 | | |
| NIPT15-672_MID026 | 20.3 | | | | |
| NIPT15-790_MID054 | 15.1 | | | | |
| NIPT15-766_MID029 | 37.0 | | | | |
| NIPT15-828_MID001 | 12.7 | | | | |
| NIPT15-1408_MID047 | 12.3 | | | | |
| NIPT15-1522_MID074 | 23.6 | | | | |
| NIPT15-1551_MID009 | 12.1 | | | | |
| NIPT15-1731_MID016 | 30.0 | | | | |
| NIPT15-1762_MID048 | 22.2 | | | | |
| NIPT15-1717_MID001 | 26.8 | | | | |
| NIPT15-1937_MID042 | 26.2 | | | | |
| NIPT15-2009_MID022 | 20.6 | | | | |
| NIPT15-2009_MID022 | 20.4 | | | | |
| NIPT15-2004_MID017 | 24.0 | | | | |
| NIPT15-2302_MID069 | 38.2 | | | | |
| NIPT15-2500_MID006 | 38.5 | | | | |
| NIPT15-2802_MID047 | 12.3 | | | | |
| NIPT15-2835_MID370 | 23.9 | | | | |
| NIPT15-2872_MID025 | 18.4 | | | | |
| NIPT15-3065_MID056 | 17.4 | | | | |
| NIPT15-3087_MID079 | 16.9 | | | | |
| NIPT15-3092_MID373 | 12.9 | | | | |
| NIPT15-3262_MID077 | 21.5 | | | | |

It should be understood that although the present invention has been specifically disclosed by preferred embodiments and optional features, modification, improvement and variation of the inventions embodied therein herein disclosed can be resorted to by those skilled in the art, and that such modifications, improvements and variations are considered to be within the scope of this invention. The materials, methods, and examples provided here are representative of particular embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

The inventions illustratively described herein can suitably be practiced in the absence of any element or elements, limitation or limitations, not specifically disclosed herein. Thus, for example, the terms "comprising," "including,"

containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Additional embodiments are set forth within the following claims.

What is claimed is:

1. A method for isolating fetal cell-free DNA (cfDNA) from a liquid biological sample from a pregnant female, said method comprising:
   a) contacting the liquid biological sample containing fetal cfDNA with a plurality of magnetic beads that reversibly bind to DNA;
   b) separating the cfDNA-bound magnetic beads from the unbound components of the liquid biological sample by inserting a magnet into the liquid biological sample to magnetically bind the cfDNA-bound magnetic beads, and removing the cfDNA-bound magnetic beads from the unbound components of the liquid biological sample;
   c) transferring the cfDNA-bound magnetic beads from the liquid biological sample to a vessel containing a wash solution;
   d) transferring the cfDNA-bound magnetic beads to a vessel containing an elution solution by inserting a magnet into the wash solution containing the cfDNA-bound magnetic beads, and depositing the magnetically-bound beads into the vessel containing the elution solution, wherein the elution solution is less than 200 µl; and
   e) separating the magnetic beads from the elution solution by contacting the vessel containing the magnetic beads in the elution solution to a magnetic plate, wherein the magnetic plate comprises a ring magnet that causes the magnetic beads to adhere to the vessel walls, and collecting the elution solution containing the fetal cfDNA, wherein the elution solution containing the fetal cfDNA has less contamination and higher yield compared to an elution solution in a vessel that was not in contact with a magnetic plate.

2. The method of claim 1, wherein the magnetic beads comprise cross-linked polystyrene.

3. The method of claim 1, wherein the surface of the magnetic beads comprises one or more functional groups that reversibly binds to DNA.

4. The method of claim 1, wherein the magnetic beads are coated with a silicon-containing coating.

5. The method of claim 1, wherein the magnet is a rod-shaped magnet.

6. The method of claim 1, wherein transfer of the magnetic beads is automated.

7. The method of claim 1 wherein the liquid biological sample is a plasma sample.

8. The method of claim 1 wherein the liquid biological sample is obtained from a human subject.

9. The method of claim 1 wherein the volume of the liquid biological sample is 0.5-2 mL.

10. The method of claim 1, wherein the volume of the elution solution is less than or about 150 µl less than or about 100 µl, less than or about 90 µl less than or about 80 µl less than or about 70 µl less than or about 60 µl less than or about 50 µl or less than or about 40 µl.

11. The method of claim 1, wherein step (a) is performed in a multiwell plate.

12. The method of claim 11, wherein washing and elution steps are performed in the same-sized multi-well plate.

13. The method of claim 12, wherein the multiwell plate is a 24-well deepwell plate.

14. The method of claim 1, wherein at least two duplicate liquid biological samples containing cfDNA are contacted with a plurality of magnetic beads.

15. The method of claim 14, wherein the cfDNA-bound magnetic beads in each duplicate sample are pooled after step (a).

16. The method of claim 1, further comprising sequentially transferring the cfDNA-bound magnetic beads to two or more wash solutions during step (c).

17. The method of claim 1, wherein the magnetic beads are uniform in diameter.

18. The method of claim 1, wherein the magnetic beads are about 1 μm in diameter.

19. The method of claim 16, wherein the washed cfDNA-bound magnetic beads are incubated in the elution solution for at least 4 minutes.

20. The method of claim 1, wherein heat is applied to the elution solution containing the magnetic beads in step (e) to elute the cfDNA.

21. The method of claim 1, wherein the liquid biological sample is prepared by removal of cells from a blood sample.

* * * * *